United States Patent [19]

Leins

[11] Patent Number: 4,559,792
[45] Date of Patent: Dec. 24, 1985

[54] THREAD CARRIER

[75] Inventor: Eberhard Leins, Filderstadt, Fed. Rep. of Germany

[73] Assignee: Sulzer Morat GmbH, Filderstadt, Fed. Rep. of Germany

[21] Appl. No.: 650,262

[22] Filed: Sep. 13, 1984

[30] Foreign Application Priority Data

Sep. 16, 1983 [DE] Fed. Rep. of Germany ....... 3333500

[51] Int. Cl.⁴ ............................................. D04B 3/06
[52] U.S. Cl. .................................... 66/125 R; 66/134; 66/142
[58] Field of Search ................. 66/125 R, 126 R, 127, 66/138, 134, 142

[56] References Cited

U.S. PATENT DOCUMENTS

| 4,196,601 | 4/1980 | Vinnemann et al. | 66/125 R |
| 4,204,414 | 5/1980 | Vinnemann et al. | 66/64 |
| 4,364,246 | 12/1982 | Leins et al. | 66/125 R |
| 4,426,855 | 1/1984 | Wells et al. | 66/125 R |

Primary Examiner—Ronald Feldbaum

[57] ABSTRACT

The invention relates to a thread carrier for a knitting machine, having at least one controllable thread gripper and an inserter (19) whose end at which the thread (16) emerges is in the form of an open channel (76). To simplify the insertion or removal of threads, the thread gripper (109) and the inserter (19) are disposed so as to be movable relative to one another such that the thread can either be inserted into the channel or removed therefrom by the thread gripper (109) itself.

11 Claims, 28 Drawing Figures

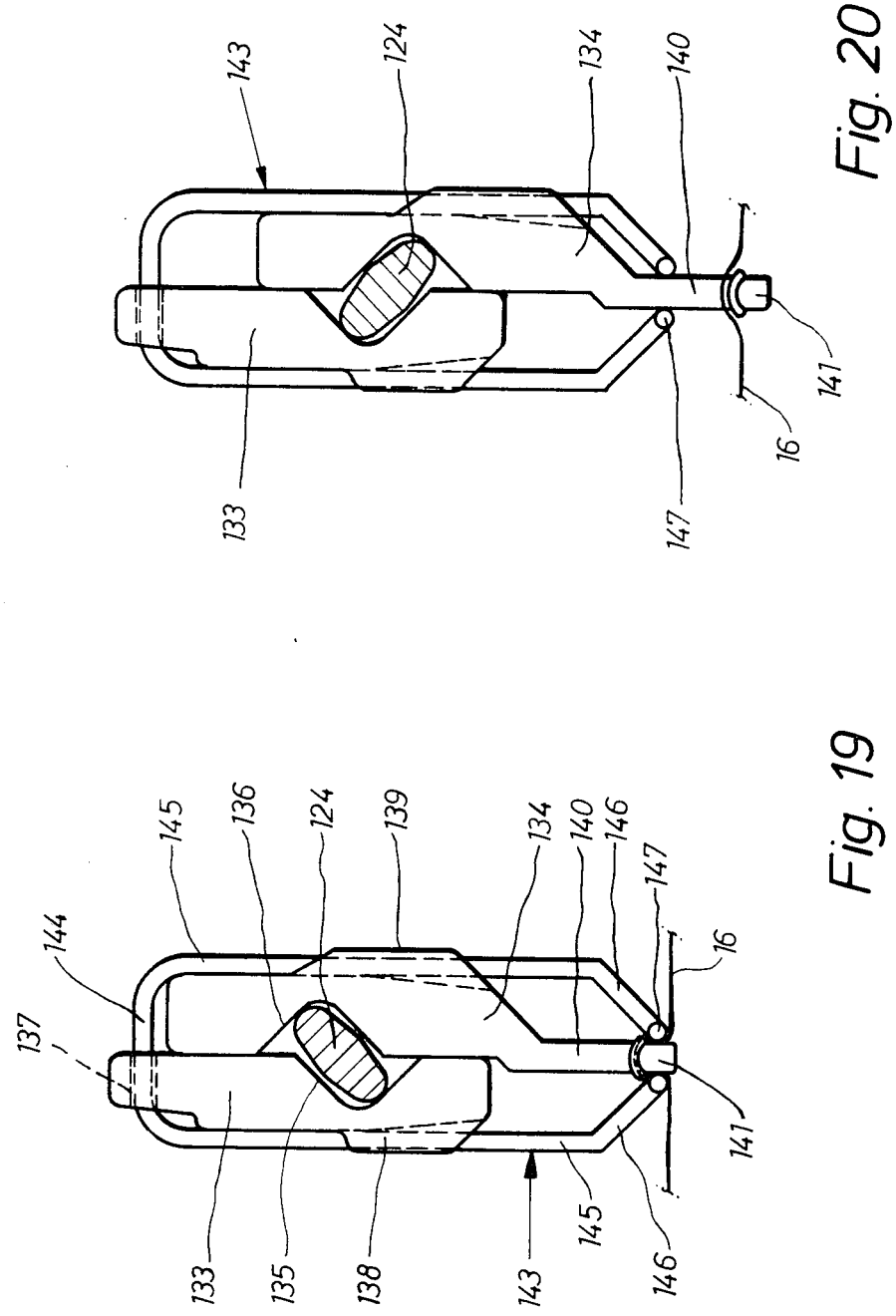

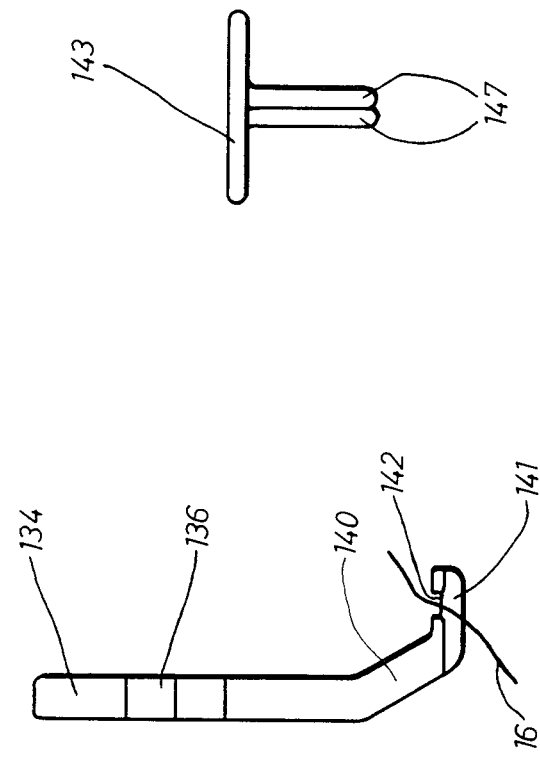

THREAD CARRIER

BACKGROUND OF THE INVENTION

The invention relates to a thread carrier for a knitting machine, having at least one controllable thread gripper and having an inserter which, at the extremity from which the thread emerges, is configured as an open channel.

Thread carriers of this kind (British Patent 1,502,370, British Publication 20 99 464) serve for feeding a thread for a certain period of time to the needles of a knitting machine and then gripping it. For this purpose the thread carriers are provided, as a rule, with at least one crank which is rocked back and forth for the insertion and removal of the thread, between the inserter and the thread gripper, while the thread gripper and the inserter are substantially fixedly disposed. Consequently difficulties arise in automatic control, especially when the thread carriers have to be carried as a whole along a needle bed, in conjunction, for example, with special flat bed knitting machines (U.S. Pat. No. 4,364,246). If what is involved is a thread carrier by which several threads are to be selectively inserted, a corresponding number of cranks and thread grippers are required. The thread carrier thus calls for a greater amount of space.

It is therefore the object of the invention to design the thread carrier of the kind defined above such that it can be controlled in a simple manner and will interfere as little as possible with access to the knitting tools of the knitting machine.

THE INVENTION

For the solution of this problem, the thread carrier defined above is characterized in that the inserter and the thread gripper are disposed movably relative to one another such that the thread can be laid into the groove or removed from the groove selectively by the thread gripper itself.

The invention offers the advantage that no additional cranks or the like are needed for the purpose of laying the thread into the inserter. The space required by the thread carrier is thus reduced, and a simple control is made possible, even in the case in which the thread carrier must be carried as a whole along a needle bed.

DESCRIPTION OF THE DRAWINGS

The invention is explained below in conjunction with the appended drawing, on the basis of an embodiment.

FIGS. 19 and 20 are front views of the slides and gripping springs of a thread gripper of the thread carrier of the invention representing the gripping and open positions;

FIGS. 22 and 23 are side views of each of the two slides of FIGS. 19 and 20;

FIG. 24 is a top view of the gripping spring of FIGS. 19 and 20;

DESCRIPTION OF A PREFERRED EMBODIMENT

Figure 1:
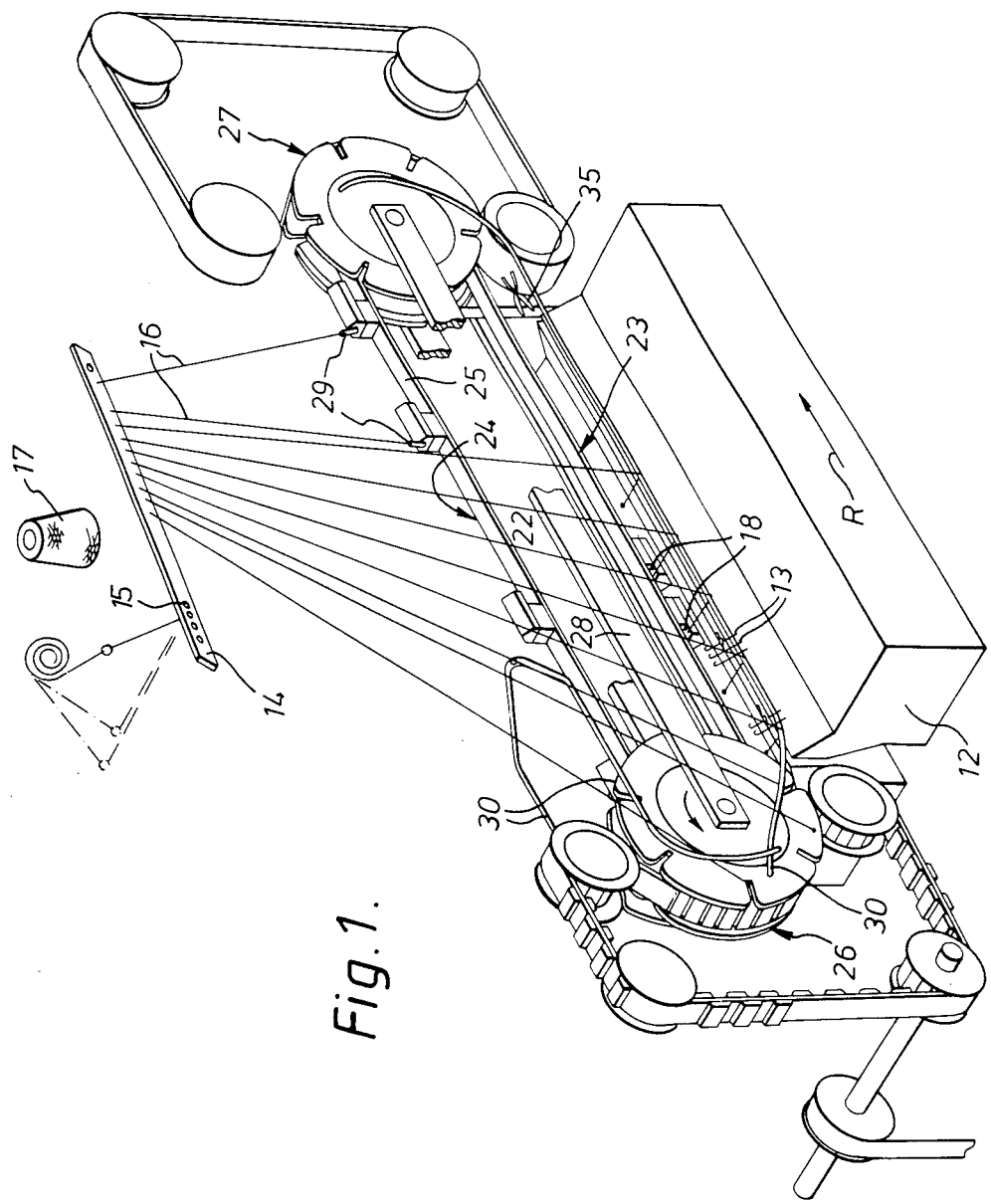
FIG. 1 is a perspective, diagrammatic representation of a knitting machine with thread carriers in accordance with the invention.

FIG. 1 represents a known flat-bed knitting machine having two needle beds 12 in whose grooves needles 13, e.g., latch needles, are guided for longitudinal displacement. Above the machine is an eyelet board through whose eyelets 15 a plurality of threads 16 are guided from stationary supply spools 17 to a plurality of thread carriers 18 having the inserters 19. For the transport of the thread carriers 18 there is provided an endless transporter 22 having a section 23 and a section 24 disposed above the operating area of the inserters 19 and parallel thereto. On section 23, the thread carriers are carried in the direction of an arrow R with their inserters pointing downwardly so that the threads 16 can be laid into the needles 13. After reaching the end of a run at the right in FIG. 1, the thread carriers 18 are carried back, with inserters 19 pointing upward, along section 24 to the beginning of the run on the left in FIG. 1, while no threads are fed to the needles 13 and the inserters 19 are moved along the return route.

The transporter 22 is formed by an endless, flexible belt 25 on which the thread carriers 18 are fastened and which is supported by two pulleys 26 and 27 whose axles are journaled at the ends of rigid rails 28. To prevent the threads 16 from entangling upon the repeated circulation of the thread carriers, they are disposed alternately on the one and on the other side of the transporter 22 by means of a rocker 29 and a plurality of guides 30. Otherwise, what is involved is preferably a flat bed knitting machine having a plurality of carriages circulating on an endless path or a flat bed knitting machine whose needles are driven by cams or cranks which are fastened with an angular offset on a revolving shaft. Further details can be found in German Offenlegungsschriften 25 31 762, 27 01 652 and 30 03 570 which are hereby expressly referred to so as to avoid further description.

The needles 13, in their extended position, define a line of operation running parallel to the upper edges of the needle beds 12, which is to be understood to be a straight line which is disposed closely above the intersection formed by the needles 13 and parallel thereto, and on which the inserters 19 must move to enable the threads 16 to be caught by the needles 13 and worked into stitches. It is assumed, in describing the thread carrier 18, that the sections of the needle beds 12 which carry the needles 13 are disposed at an angle of about 45° from the horizontal floor and have parallel as well as horizontal upper edges. The statements that follow concerning the position, arrangement or location of various parts of the thread carrier 18 relate, therefore, to the position which the thread carrier assumes when the inserter 19 runs through section 23 of such a knitting machine. The portions which in this case lie forward (on the right side in FIG. 1) or rearward (on the left in FIG. 1) in the direction of movement will be referred to throughout this description as "front" and "rear" portions, respectively. Accordingly, portions adjacent the needle intersection will always be called "lower" portions, and those remote from the needle intersection will be called "upper" portions. Lastly, those portions which, when the inserters 19 pass along the line of operation, are on the right and left of the vertical plane passing through the needle intersection will be called "right" and "left" portions, respectively. If the thread carrier of the invention is used on a machine with a different arrangement of the needle beds or needles, these designations would have to be amended accordingly.

The embodiment of the thread carrier 18 in accordance with the invention will now be described with reference to FIGS. 2 to 6. It is assumed that any thread carrier 18, as long as its inserter 19 is within the operating zone, will always be moving in the direction of the arrow R, i.e., from left to right in the drawing.

A carrier 33, which consists of an upper part 34 and a lower part 35, serves to transfer the movement of the transport belt 25, which is in the form of a cog belt, to the thread carrier 18. The upper part 34 and the lower part 35 have flange-like wings through which mounting screws 36 pass and which, if desired, are provided with metal washers 37 to prevent scoring if they are made from plastic.

The upper part 34 has a U-shaped cross section (FIG. 5) and consists of two lateral, parallel guides 38 whose lower ends are joined by a transverse portion 39, the two guides 38 being provided with central guiding grooves 40 beneath which the transport belt 25 is disposed. The thread guide 18 is joined to the transport belt 25 by means of pins 41 which enter into bores formed in the guides 38 and fit between two cogs of the transport belt 25 such that no play can occur in the direction of transport. To prevent the screw fastening produced by screw 36 from being too severely stressed, the ends of at least one pin 41 extend also into recesses 42 (FIG. 5) formed in the lower part 35, thereby directly coupling to the transport belt the lower part 35 bearing the thread carrier 18. To prevent the pins 41 from jumping the cogs of the transport belt 25, support pins 43 are provided, which extend through bores formed in the guides 38 and engage the broad, cogless side of the transport belt 25.

Within the operating area, the upper part 34 rides on a track 44 (FIG. 5) which enters into the guiding grooves 40, each of which is provided with lead-in bevels 45 (FIG. 3) and guide the thread carriers 18 within section 23 on a course precisely parallel with the needle intersection. The track 44 is fastened to a beam 46 which, at the beginning of section 23, passes between the two guides 38 and guides them laterally so as to prevent the thread carriers 18 from tipping. For this purpose the guides 38 can also be provided with lead-in bevels at their front ends. The beam 46 is suspended from a bracket 47, which is fastened, for example, to the rigid rails 28 (FIG. 1).

Figure 3:
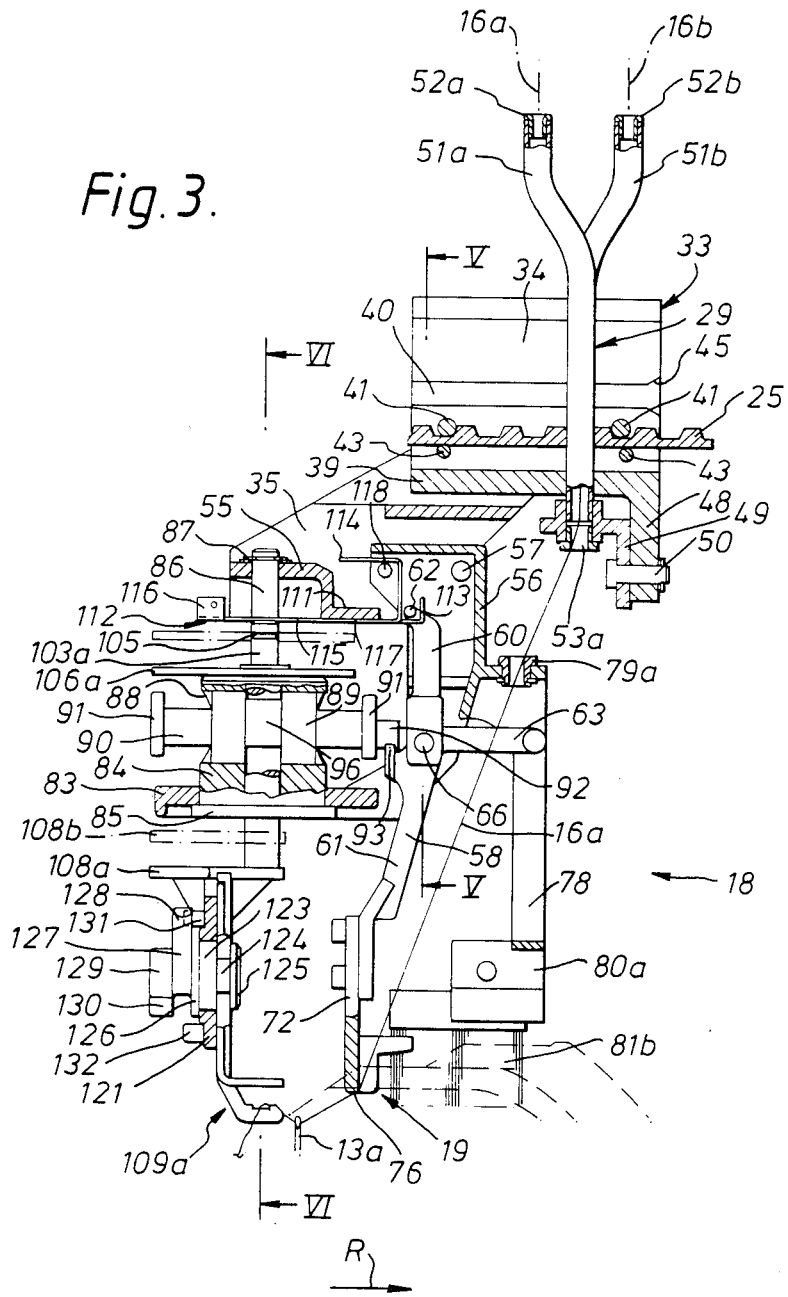
FIG. 3 is a partially sectional side elevation of the thread carrier of FIG. 2, the section line being taken through its central plane running parallel to the transport direction, and the thread grippers being shown in a different position.
Figure 11:
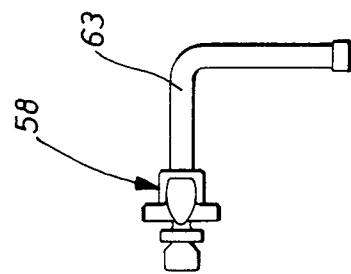
FIGS. 9 to 11 are side, front and top views of a control lever of the thread carrier of the invention.

The bottom part 35 has two lateral walls 54 (FIG. 5) and a supporting plate 55 (FIG. 3). Between the lateral walls 54 a box 56 is fastened by screws 57. In this box is pivotingly mounted a control lever 58, which is represented in three views in FIGS. 9 to 11. The control lever 58 contains in its central portion a bore 59 for pivotal mounting, and above and below this bore 59 it contains the arms 60 and 61, respectively. The upper arm 60 is provided at its extremity with two studs 62 pointing outward laterally parallel to the axis of the bore 59. In its middle portion the control lever 58 has a lateral crank arm 63 which starts out parallel to the axis of bore 59 and then is bent such that the central axis of its free end is substantially parallel to the axis of bore 59. The lower arm 61 of the control lever 58 has at its free end two taps 64.

Figure 5:
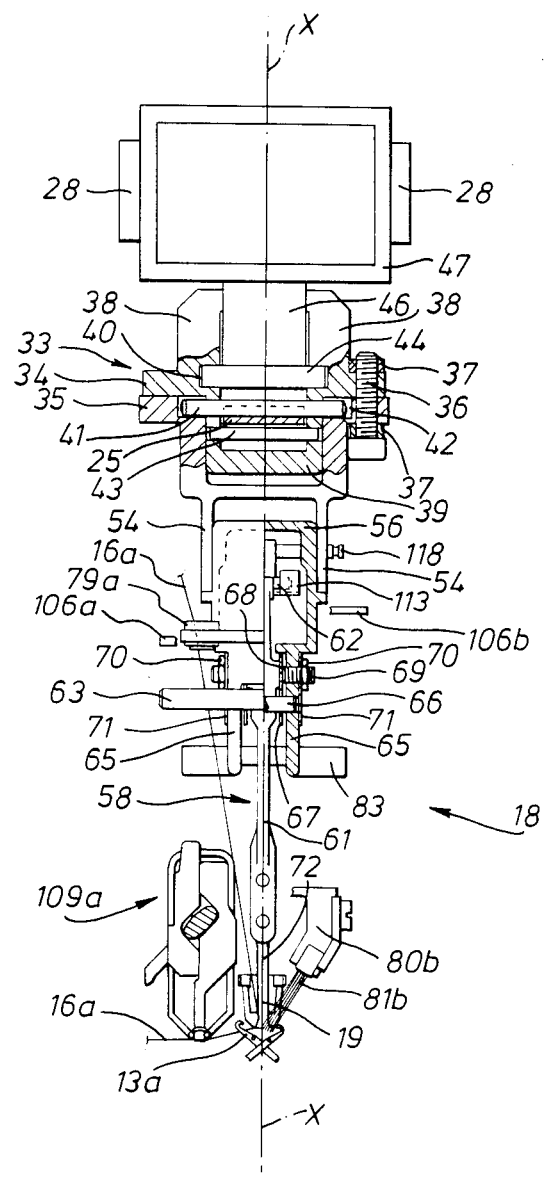
FIG. 5 is a front elevational view of the thread carrier of FIG. 2, partially in section along line V—V of FIG. 3.
Figure 10:
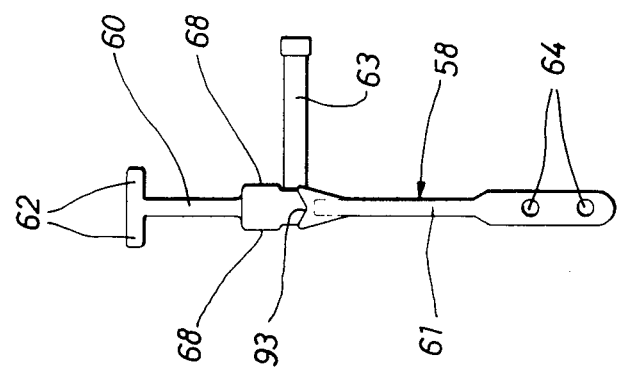
Figure 9:
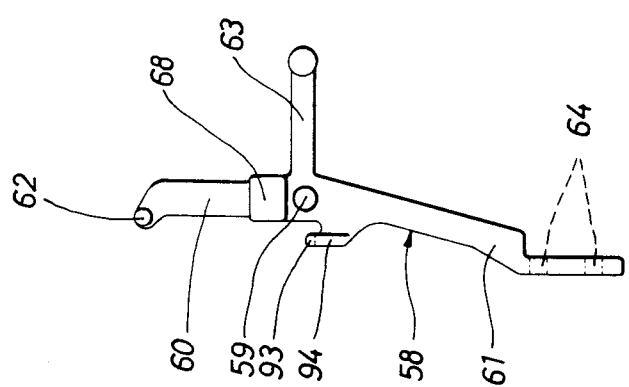

As seen in FIG. 5, the control lever 58 is pivotally mounted between two lateral walls 65 of the box 56 on a pivot shaft 66 which passes through bores in these lateral walls 65 and bore 59. Pivot plates 67, through which pivot shaft 66 also passes, and which engage the bearing surfaces 68 of control lever 57, which are formed, as seen in FIGS. 5, 9 and 10, on a thickened portion of arm 60, serve for the lateral adjustment of the control lever 58 on the pivot shaft 66. At the bearing surfaces 68, an adjusting screw 69 thrusts against the outside of each of the pivot plates 67, each adjusting screw 69 passing through a tap in the corresponding lateral wall 65 and being provided with a counternut 70. Between the counternut 70 and the lateral wall 65 there is disposed an additional pivot plate 71 which covers the bores in lateral walls 65 which accommodate the pivot shaft 66. All of the pivot plates 67 and 71 moreover engage projecting edges of the lateral walls 65 (FIG. 2) such that they are substantially held against rotation. As a result of this mounting, the control lever can be adjusted axially of the pivot shaft 66 by means of the adjusting screw 69 in a clearance-free manner for the purpose of compensating for manufacturing tolerances, the inner pivot plates 67 only just touch the bearing surfaces 68 and thus provide a good frictional support, and the counternuts 70 cannot loosen after the adjustment has been made.

Figure 7:
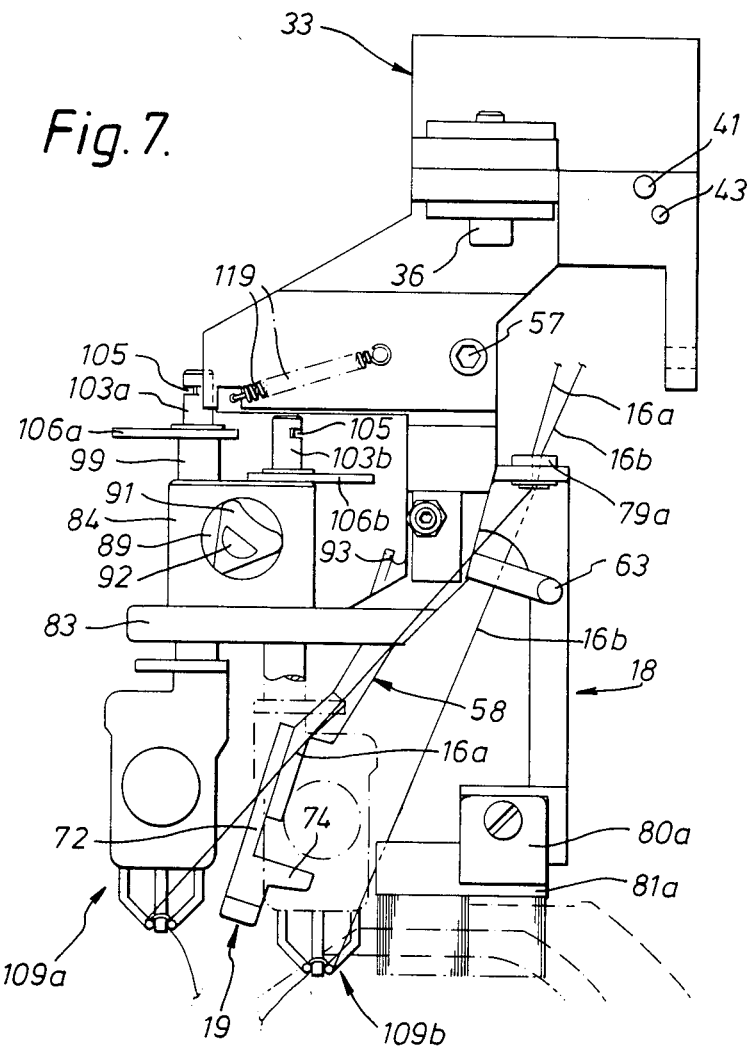
FIG. 7 is a side elevational view of the thread carrier of FIG. 2 with the thread grippers in a third position.
Figure 14:
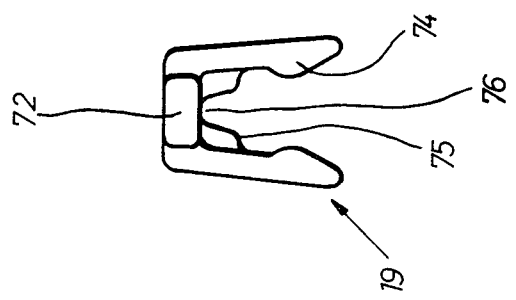
FIGS. 12 to 14 are front, side and top views of an inserter of the thread carrier of the invention.
Figure 13:
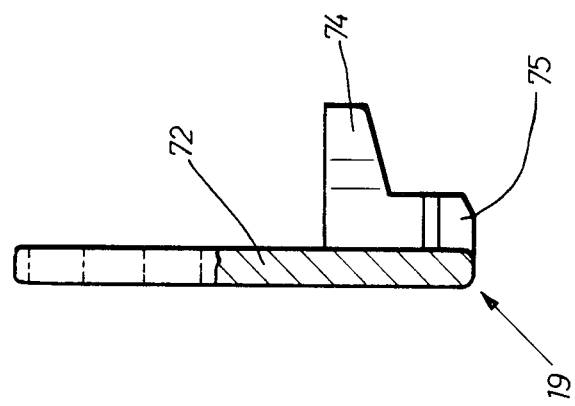
Figure 12:
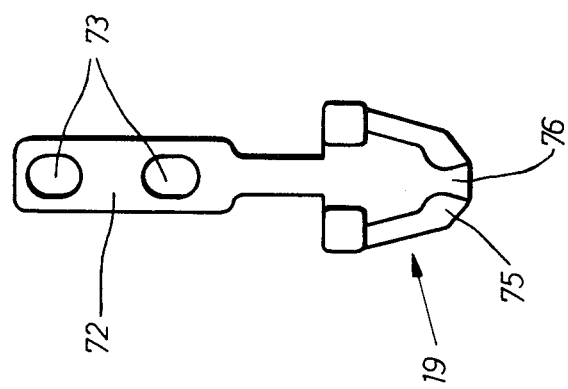

A downwardly projecting plate 72, which bears at its bottom end the inserter 19 of the thread carrier 18 and can be adjusted precisely for height by means of the slots 73 which contain the mounting screws, is fastened to the arm 61 of the control lever 58 by screws driven into the taps 64. The inserter 19, which is shown in three views in FIGS. 12 to 14, has on its front end a fork 74 shaped in the manner of a lead-in guide, and in its bottom a groove 76 open at top and bottom whose central axis, when the control lever 58 is in the normal position visible in FIG. 3, is precisely in a central plane X of the thread carrier 18 just above the needle intersection (as seen in FIG. 7), and, like the fork 74, opens frontwardly and is transported within the operating area.

On the front end of the box 56 there is fastened a vertically disposed, downwardly extending supporting arm 78 which has at its upper end two thread eyelets 79a and 79b (FIG. 8), but on its lower end it has two mounts 80a and 80b each for holding a brush 81a, 81b, which opens the needle latches or holds them open. These brushes 81a and 81b precede the thread carrier 18 and serve especially for covering the open needle latches and keeping them open. In FIGS. 2 to 4 and FIG. 7, only parts 79a, 80a and 81a are visible, while FIG. 5 shows parts 80b and 81b; the parts that have the suffix a are disposed on the right and those with the suffice b are disposed on the left of the central plane X of the thread carrier.

On a bottom portion of the box 56 there is disposed a horizontal, inwardly extending support plate 83. In a center bore of the support plate 83 there is mounted rotatably on a vertical axis of rotation a drum 84 whose bottom, widened margin 85 (FIG. 3) engages the support plate 83, and which bears at its top a coaxial, cylindrical shaft 86 which is journaled in a bore in the support plate 55 of bottom part 35 and is axially held in place by a snap ring on the end remote from the drum 84. The drum 84 has a bearing bore 88 for the rotatable mounting of a shaft 89 at whose both ends heart-shaped cams 91 are fastened on intermediate members 90. On the front face of the control cam 91 situated on the right in FIG. 3 there is also provided a semicircular catch 92. The arrangement is contrived such that the catch 92, when the drum 84 is in the position represented in FIG. 3, in which both the axis of shaft 89 and the axis of rotation of drum 84 are situated in the central plane X, rests in a cradle 93 formed on a rearward projection 94 of the control lever 58 whose pivot axis is preferably perpendicular to the central plane X.

Figures 15, 16:
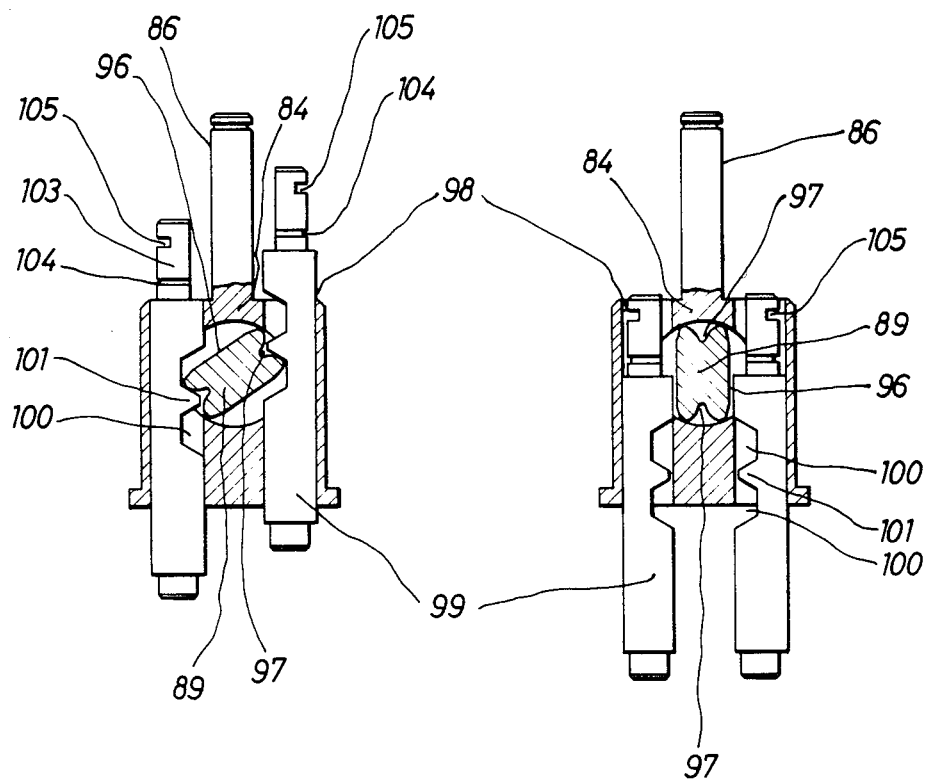
FIGS. 15 and 16 are enlarged sections through a drum of the thread carrier of the invention, taken along line VI—VI of FIG. 3.

As represented in FIGS. 3, 15 and 16, the shaft 89 is provided in its central portion and on both sides of its central axis with a constriction 96 and on each side thereof a tooth gap 97 situated radially outwardly which gives the middle part of shaft 89 the form of a pinion. The drum 84 furthermore has two longitudinal bores 98 parallel to the drum axis, whose axes are parallel with one another and disposed symmetrically on either side of the shaft 86. A cylindrical rack 99 is displaceably mounted in each of the longitudinal bores 98. Each rack 99 is provided in a central section with two recesses 100 one on each side of a tooth 101. The arrangement is such that the two longitudinal bores 98, shown in FIGS. 15 and 16, cut slightly into the cavity made by the bearing bore 88 and each rack 99 passes partially through the bearing bore 88 at its margins.

When the shaft 89 is in the rotational position shown in FIG. 16, the racks 99 are introduced into the longitudinal bores 98 from the bottom, while the constrictions 96 have left the longitudinal bores 98 open. If the racks 99 assume, say, the position shown in FIG. 15, the shaft 89 is rotated such that the teeth 101 now reaching into the bearing bore 88 engage the tooth gaps 97.

At the upper ends the racks 99 have coaxial, but only approximately semicylindrical projections 103a and 103b of reduced cross section which have in a lower portion an annular groove 104 and at its upper ends a lateral cross groove 105. A coding plate 106a or 106b is drawn onto each projection 103 and has a corresponding semicircular central bore and therefore is held unrotatably on the projections. The coding plates 106 are installed downwardly after the introduction of racks 99 into the longitudinal bore 98, until they rest on the upper shoulders of the racks 99, and then they are axially secured by means of snap rings 107 forced into the annular grooves 104. A holder 108a, 108b, for holding a thread gripper 109a, 109b, is fastened to the bottom end of each rack 99, the arrangement being such that the upward and downward displacement of the racks is limited in each case by the coding plate 108 encountering the top of the drum 84, and that, when assembly is complete, the teeth 101 will always remain in engagement with the corresponding tooth gaps 97. By rotating the shaft 84 in the one or the other direction, the racks 99 can thus be moved upwardly and downwardly, simultaneously, but always in opposite directions.

Figure 2:
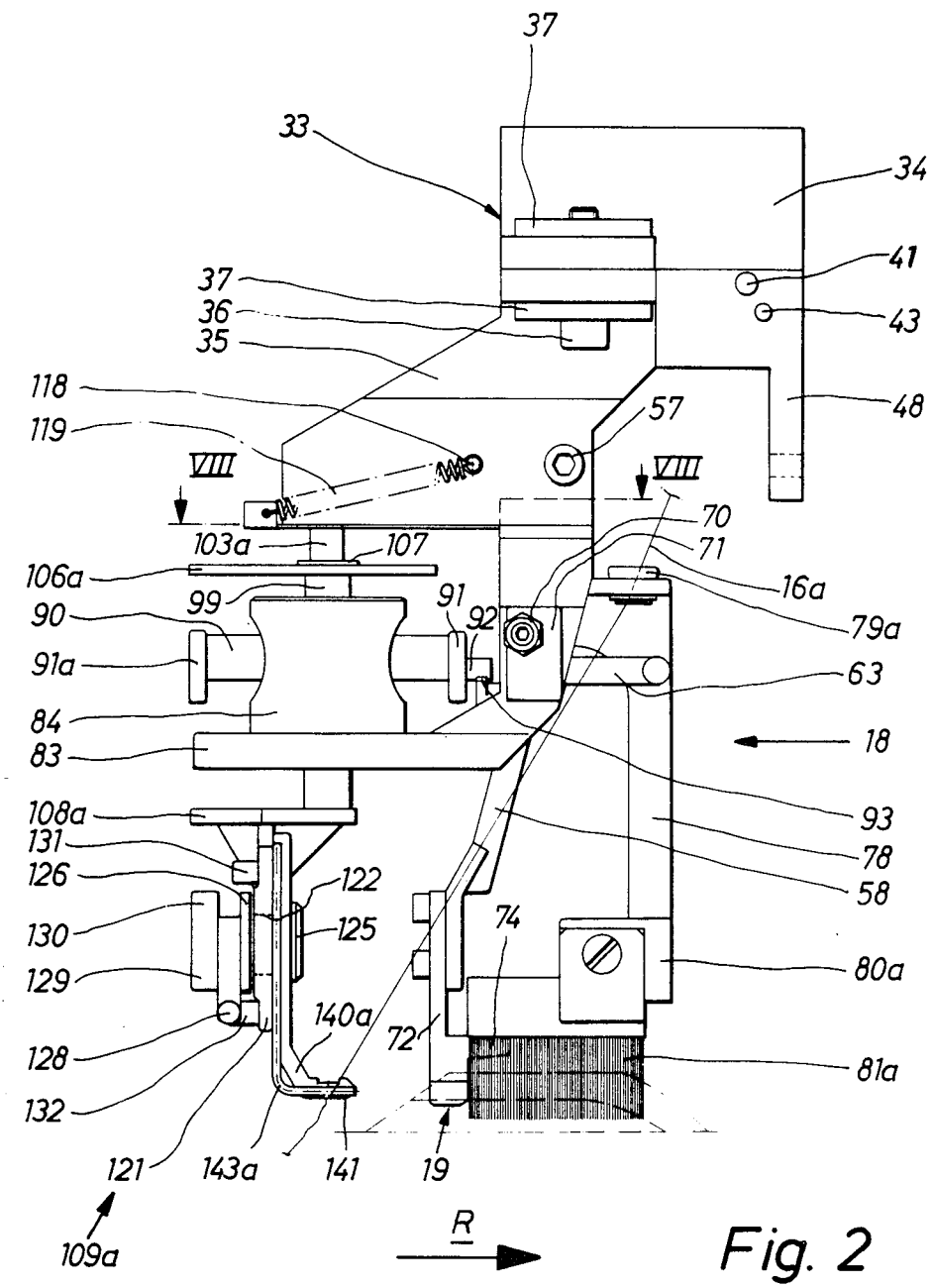
FIG. 2 is a side elevational view of a thread carrier of the invention taken perpendicularly to its transport direction.
Figure 6:
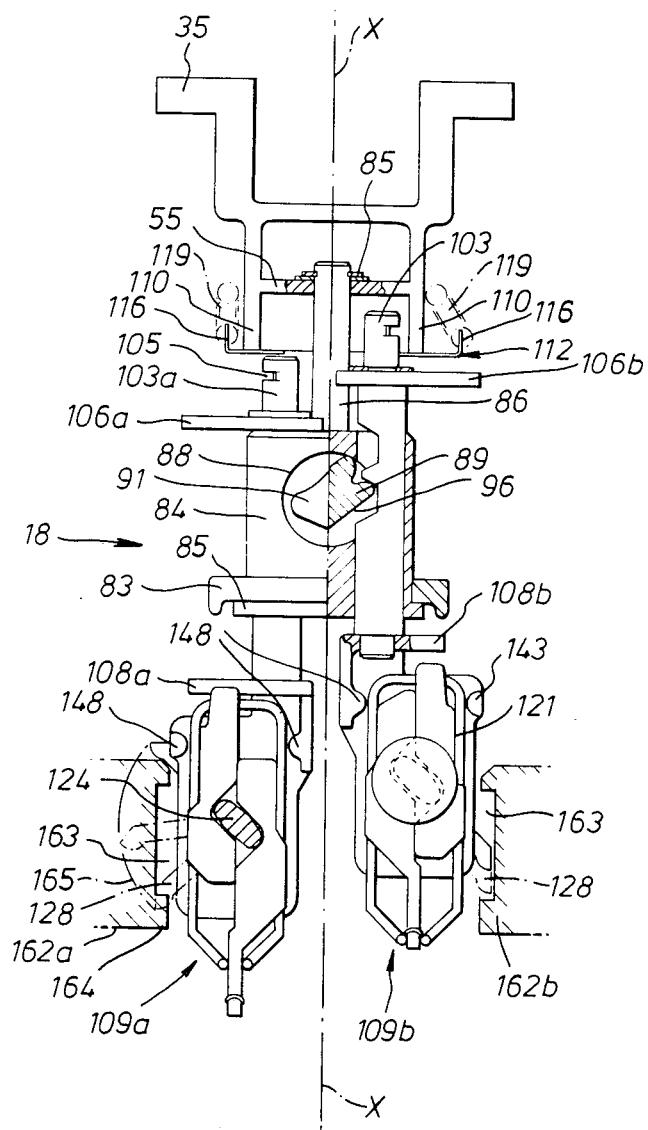
FIG. 6 is a front elevational view of the thread carrier of FIG. 2, partially in section along line VI—VI of FIG. 3.
Figure 17:
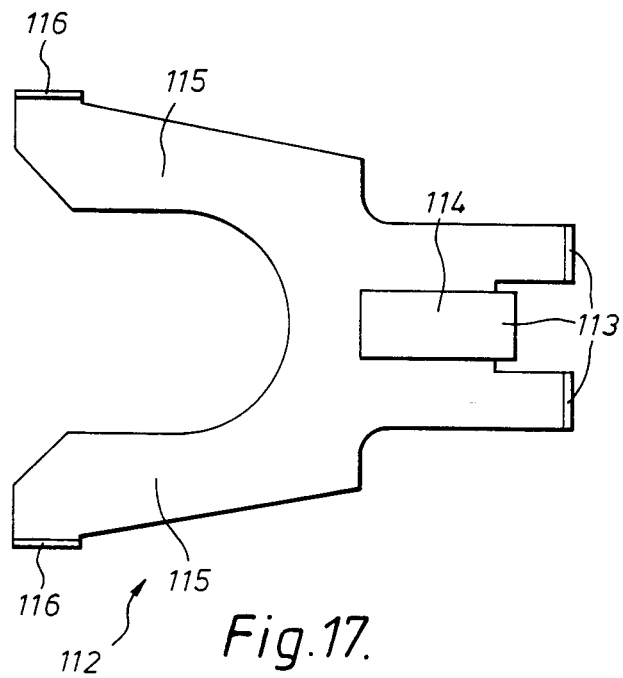
FIGS. 17 and 18 are the top view and a side view of an arresting slide of the thread carrier of FIG. 2.
Figure 18:
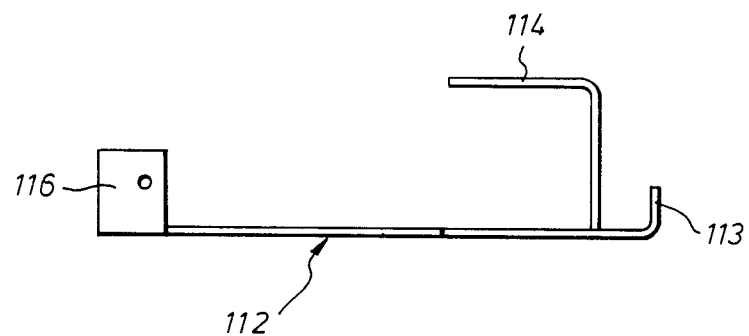
Figure 22:
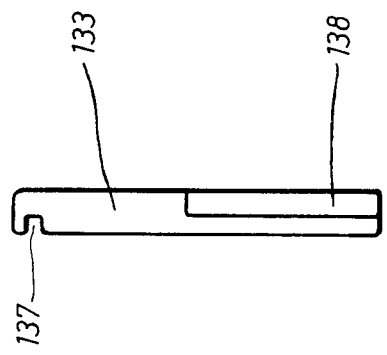
Figure 21:
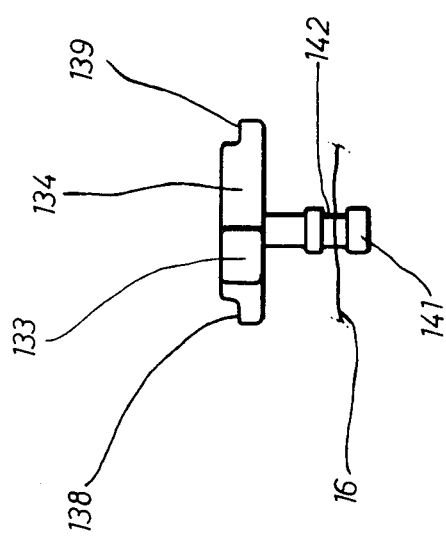
FIG. 21 is a top view of the parts represented in FIGS. 19 and 20.

Referring now to FIGS. 3 and 6, the bottom part 35 of carrier 33 has two parallel portions 110 projecting downwardly from the supporting plate 55; their bottom edges, together with the bottom of a portion 111 parallel to the supporting plate, serve as abutment and slide surfaces for an arresting slide 112. This arresting slide 112 is represented in FIGS. 17 and 18 in two views. It consists of a thin piece of sheet metal having at its front end two tabs 113 bent upwardly at about 90° and disposed on either side of a hanger 114. On its rearward end the arresting slide 112 is provided with a central cutout leaving two rearwardly extending arms 115 constituting a fork. The distance between the fork arms 115 is approximately equal to the distance between the bottoms of the two transverse grooves 105 in the projections 103. Moreover, the fork arms 115 are joined to the tabs 113 and the hanger 114 by a midsection 117 which, on the side facing the fork arms 115 runs along an arc whose radius amounts to half of this distance. At the rear extremities of the fork arms the tabs 116 are provided, which contain bores and are bent upwardly at about 90°. In accordance with FIG. 3, the arrangement is such that the arresting slide 112 engages the parallel portions 110 of bottom part 55 with its fork arms 115 and engages the bottom portion 111 with its midsection 117, while at the same time the tabs 113 engage each a stud 62 of the control lever 58, while the hanger 114 engages and hangs on a pin passing through the sidewalls of the bottom part 35 and of the box 56. The pin 118 serves on the one hand for the additional fixation of the box 56 on the bottom part 35, and on the other hand it serves, with its end projecting from the bottom part 34, as a means for the attachment of one end of each tension spring 119 whose other ends are attached to the bores in the tabs 116 (FIG. 2). The tension springs 119 draw the arresting slide 112 against the parallel portions 110 and bottom portion 111, and, by means of the studs 62 situated between the tabs 113 and the hanger 114, they simultaneously bias the control lever 58 in the clockwise direction as seen in FIG. 3.

Figure 4:
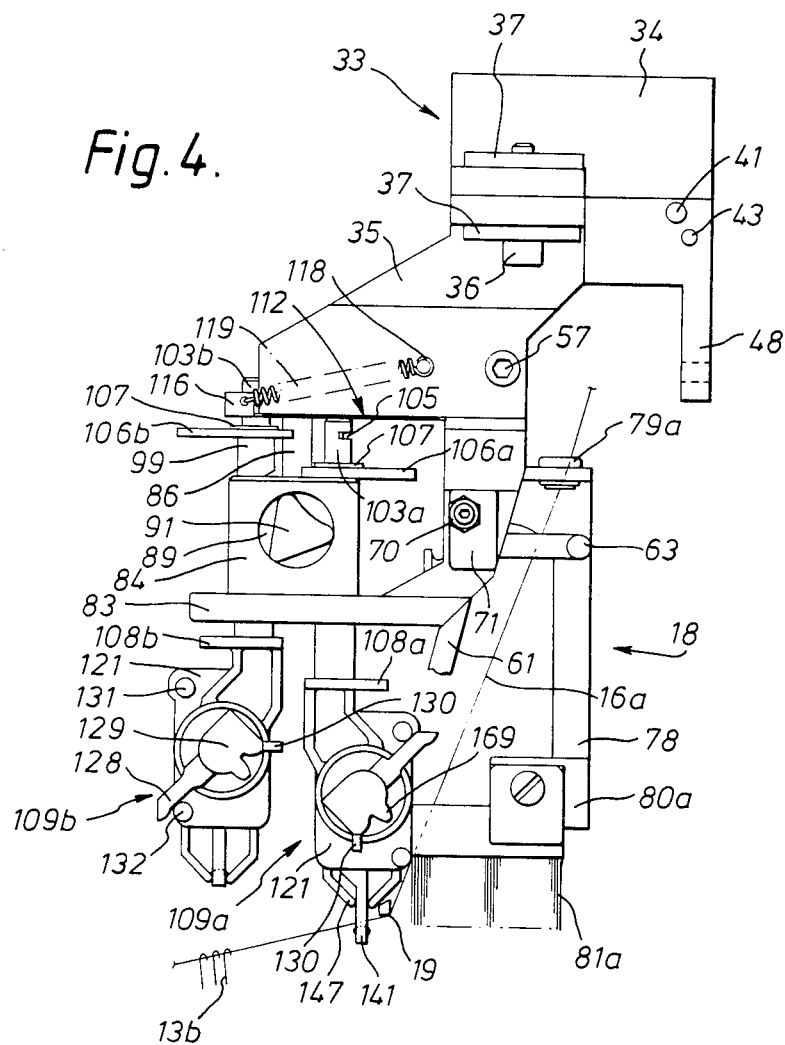
FIG. 4 is a side elevational view of the thread carrier corresponding to FIG. 2 with the thread grippers in a different position.
Figure 8:
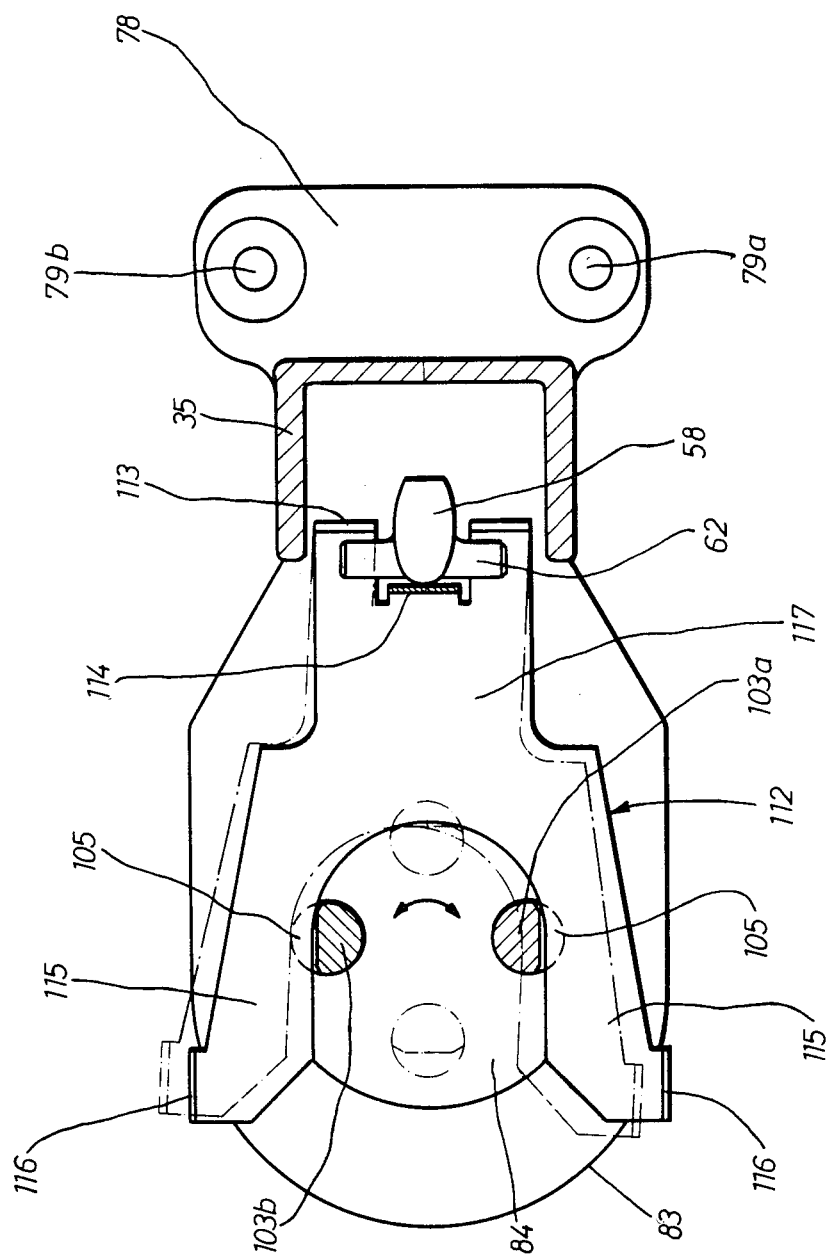
FIG. 8 is a plan view partially in section along line VIII—VIII of FIG. 2.

The arresting slide 112 is so configured and disposed that the transverse grooves 105 created on the projections 103 are at the same level as the fork arms 115 when the two coding plates 106 are in their central position at the same level (see FIG. 2). The fork arms 115 therefore enter the transverse grooves 105 when drum 84 revolves, as indicated in FIG. 8 by the solid-line position of the arresting slide 112. This locks the racks 99 and with them the thread grippers 109 against accidental vertical movements. If, however, the coding plate 106b is in its raised position, for example, as indicated in FIGS. 4 and 6, and therefore the other coding plate 106a is in its lowered position, then, when the fork is pushed forward the upper end of the projection 103a below it will be situated just underneath the arresting slide 112, while the other projection 103b projects into the space between the fork arms 115 and thus pushes the arresting slide 112 slightly to one side, as indicated in FIG. 8 by the broken-line position of the arresting disk 112. Therefore, in this position any accidental vertical displacement of the thread grippers 109 is blocked by the fork arm 115 engaging the projection 103a.

The thread grippers 109 are represented in different positions in FIGS. 2 to 6. They contain a mounting plate 121 extending substantially vertically downward, which is fastened to the corresponding holder 108 and is provided with a central bore 122 (FIG. 2) in which a circular pivot 123 is rotatably mounted. On the front end of this pivot 123, which projects from the central bore 122, there is provided a guide disk 125 which has a smaller cross section than the central bore 122. The pivot 123 has on its back a flange 126 on the back of which is provided a projection 127 having an actuating finger 128, and on the back of the projection 127 there is provided an additional projection 129 with an additional actuating finger 130. The rotatory movement of the pivot 123 is limited by two abutments 131 and 132.

After the pivot 123 has been inserted into the central bore 122, with its flange 126 engaging the back of the mounting plate 121, the shift cam 124 is rotated to an approximately 45° position (FIGS. 19-20). Flat slides 133 and 135 of substantially rectangular basic shape are thus shifted by the two sides of the shift cam 124 between the mounting plate 121 and the guide disk 125. Each slide, as represented in FIGS. 19 to 24, has a triangular notch 135, 136, on one longitudinal side, in which notch the shift cam 124 completely disappears in the arrangement represented in FIGS. 19 and 20, so that the slides 133, 134, engage one another at their longitudinal sides. The slide 133 is provided at its upper margin with a transverse groove 137 on its back, and on its longitudinal side opposite the notch 135 it is provided with a lip 138 projecting laterally from its face. The slide 134 is provided on its longitudinal side opposite the notch 136 with a lip 139 projecting laterally from its face, and at its bottom it is provided with a forwardly slanting prolongation 140 disposed at an angle to its broad sides. This prolongation carries a forwardly projecting, substantially horizontally disposed gripping finger 141 having in a central portion an indentation 142 in which the thread comes to lie during the gripping action (FIGS. 21 and 23) and therefore will be unable to slip forwardly.

The thread gripper 109 is completed by a spring clip 143 which, as represented in FIGS. 19, 20 and 24 is bent to an approximate rectangle and is pressed from the front onto and behind the two shifting slides 133 and 134 so that its upper loop 144 comes to rest in the transverse groove 137 and its two legs 145 come to rest between the lips 138 and 139 and the mounting plate 121. At its bottom end the spring clip 143 has two portions 146 slanting toward one another whose ends are bent forward at 90° and form gripper jaws 147. The gripper jaws 147 are biased resiliently against one another and, in the gripping position represented in FIG. 19, they engage the gripping fingers 141 parallel and from below, so that a thread 16 lying between them will be securely gripped. If the shift cam 134 is rotated about 90° clockwise, the slide 133 will be lifted and slide 134 lowered, so that accordingly the spring clip 143 coupled to the slide 133 will be raised upwardly, and with it the gripper jaws 147, but the gripping fingers 141 will be shifted downwardly to the open position of the thread gripper 109 (FIG. 20), releasing a previously held thread 16. At the same time, the shift cam 134, in passing from the one position to the other, will, by spreading the slides 133 and 134 laterally apart, produce a slight spreading of the spring clip 143, making it easier for the gripper jaws 147 to slip over the lateral projections formed by the indentation 142. The end position of the shift cam 124 shown in FIG. 19 corresponds to the engagement of the actuating finger 128 with the bottom abutment 132, while the end position of the shift cam 124 shown in FIG. 20 corresponds to the engagement of the actuating finger 128 with the upper abutment 131. The spring clip 143 serves simultaneously to secure the position of the assembly formed by the pivot 123, shifting cam 124, guide disk 125, flange 128 and projections 127 and 129 on the mounting plate 121, without the need for additional fastening means. On its front side the mounting plate 121 is additionally provided with two guiding cams 148 which during the shifting actions engage the legs 145 of the spring clip 143 and guide them laterally. Otherwise the slides 133 and 134 are guided with sliding friction between the mounting plate 121 and the guide disk 125.

Figure 25:
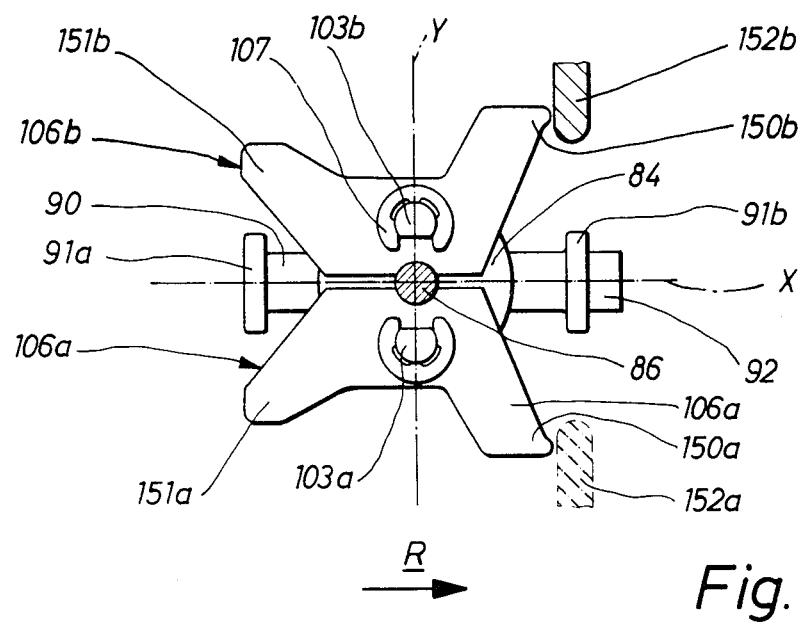
FIGS. 25 and 26 are enlarged top views of coding plates of the thread carrier of the invention.
Figure 26:
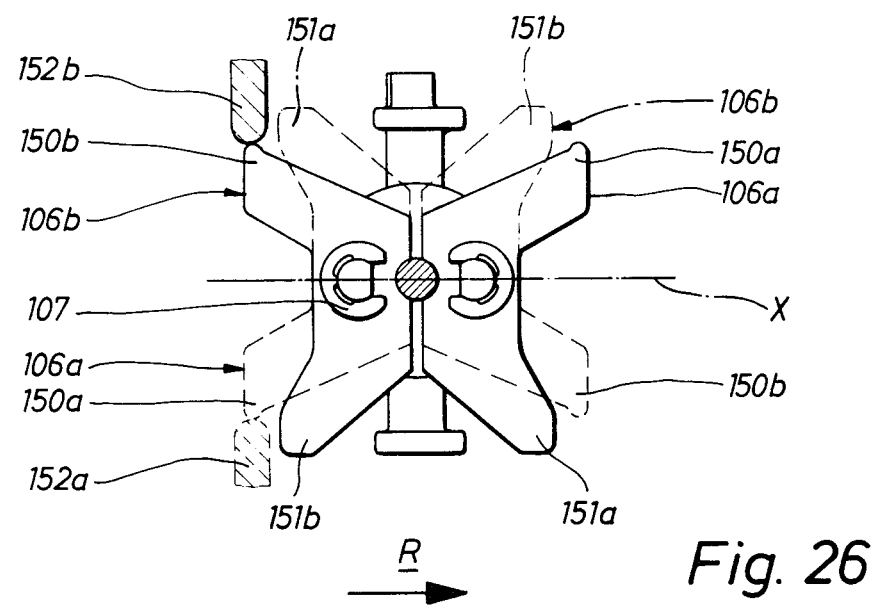

The configuration of the coding plates 106a and 106b is represented in FIGS. 25 and 26. They consist of flat plates having at their front end and back end the arms 150a and 151a, and 150b and 151b, respectively, extending outwardly from the central plane X of the thread carrier. The arms 150b and 151b are so configured that, in the position represented in FIG. 25, the maximum distance between arms 150 and the central plane X is greater than the corresponding maximum distance between arms 151, while at the same time the maximum distance of the arms 150 from a vertical plane Y through the axis of rotation perpendicular to the central plane X is smaller than the corresponding maximum distance between the arms 151. The difference in the distance is so great that a cam 152a, 152b, brought into the path of the coding plates, by acting on a front arm 150a or 150b will turn the coding plates 106a and 106b precisely 90° into one of the two positions shown in FIG. 26 (solid or broken lines), or that the arm 150 acted upon by this cam 152 will be situated, upon disengagement from this cam (FIG. 26), in a manner corresponding to a precise 90° rotation of the coding plate. The same applies if the coding plates 106 are to be turned precisely 90° back to the position shown in FIG. 25 by a cam acting on the arms 151a and 151b which then are farther away from the central plane X.

For the automatic control of the thread carriers 18 circulating with the transport belt 25, control stations, known in themselves (German Offenlegungsschrift 30 03 570), are disposed at the beginning and at the end of the working section, which have cams and cam followers whereby action is exercised on the crank arm 63, the control cams 91, the coding plates 106 and, in some cases, the actuating fingers 128 and 130, and which are best fastened to the rigid rail 28 or to a component connected therewith. The required cams and cam followers are represented in FIGS. 27 and 28.

The described thread carrier operates as follows:

Each thread carrier 18, before entering the control station at the beginning of the working section, assumes the gripping position seen in FIG. 2, wherein the catch 92 lies in the cradle 93. Consequently, on the one hand the control lever 58 is locked against the force of springs 119 and on the other hand the drum 84 is secured against rotation. The fork 74 is in its forwardly shifted position, while the thread grippers 109 are disposed symmetrically with both sides of the central plane of the thread carrier, with the gripping fingers 141 pointing forward.

Figure 27:
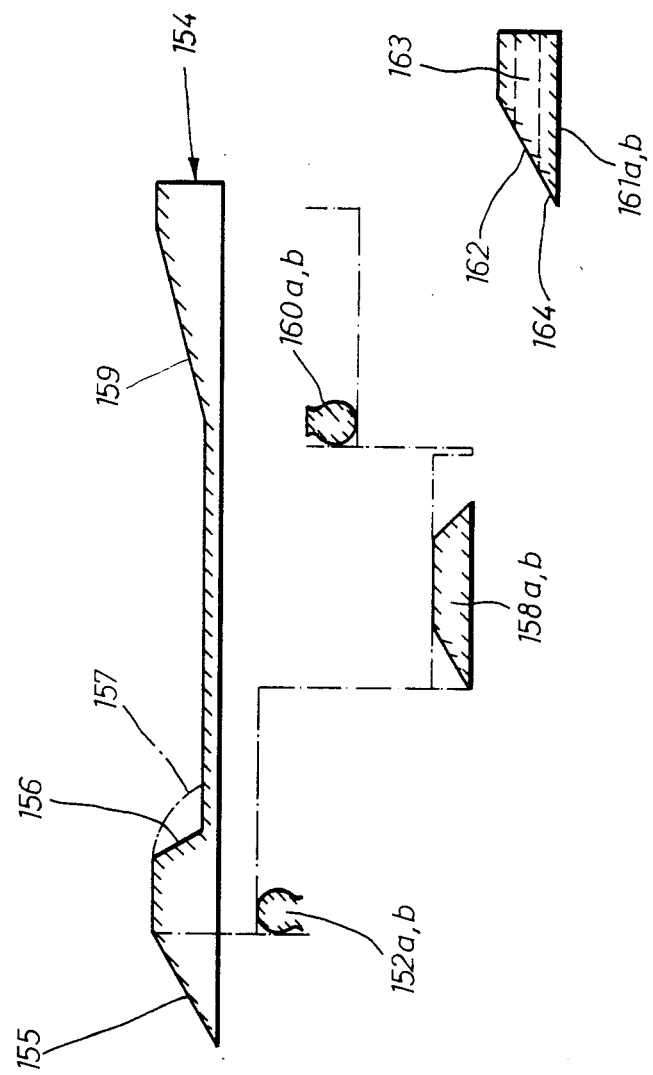
FIGS. 27 and 28 are diagrams of the cams required for the control of the thread carrier of the invention at the beginning and end, respectively, of the working section of a knitting machine equipped with the thread carrier of the invention.
Figure 28:
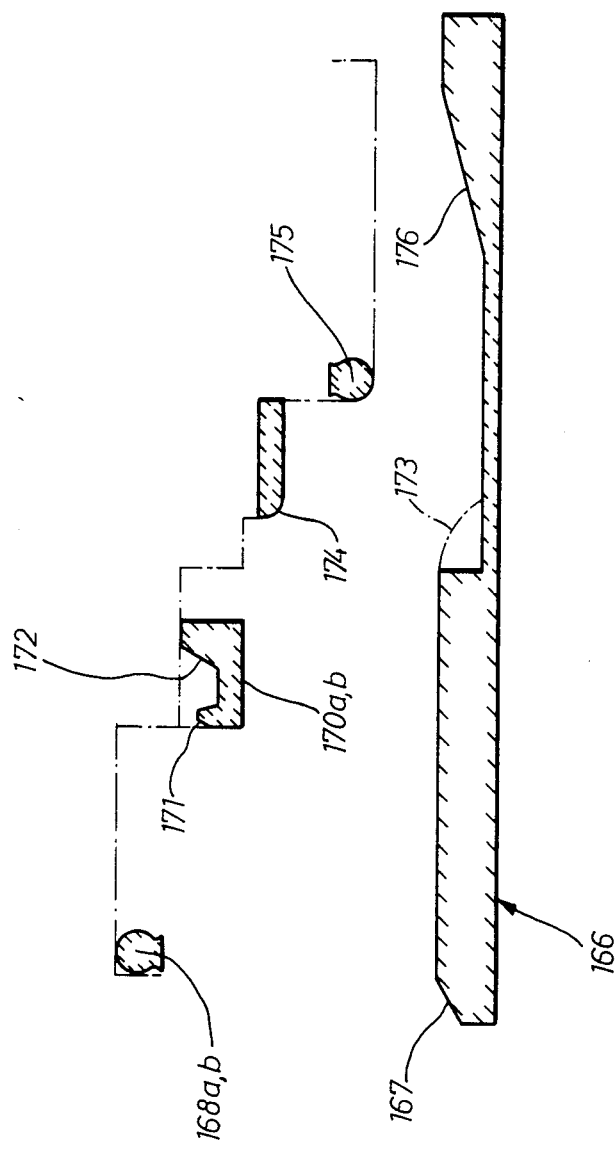

The free end, pointing to the right, of the crank arm 63 of the thread carrier now runs onto a fixed cam 154 represented in its side elevation in FIG. 27, which shifts the control lever 58 slightly such that the cradle 93 is lowered and the catch 92 is released. If no operation is to be performed with either of the two threads carried by the thread carrier, the crank falls back into the locking position under the influence of the tension springs 199, after leaving cam 154.

If, however, knitting is to be performed with the thread carrier, a choice must first be made as to which of the two threads 16a and 16b is to be inserted. The selection is made by means of one of the two cam followers 152a and 152b (FIGS. 25 and 26) which are disposed one on each side of the central plane X in a low position, and can be brought by an operating means not shown, e.g., a magnet, to a middle position in which they are disposed at the level of the coding plates 106a and 106b which are in the middle position. If cam follower 152a, represented in a top view in FIG. 27, is selected, therefore, only the coding plate 106a will engage this cam follower, while the other coding plate 106b remains unaffected. As a result, when it passes the cam follower 152a, the drum 84 will rotate 90° and therefore both of the thread grippers 109a and 10b will be disposed one behind the other to the left of the central plane X, with the thread gripper 109b leading.

Shortly after the drum begins to turn, the crank arm 63 is released by a descending portion 156 of cam 154, so that the control lever 58 is rocked by the effect of the tension springs 119 along a line 157 (FIG. 27) to the position seen in FIG. 7, in which the fork 74 is disposed behind the thread 16b held by the thread gripper 109b. The thread 16a is disposed outside of the range of action of the fork 74.

The heart-shaped control cams 91, which are disposed transversely of the transport direction due to the drum rotation, with their apexes pointing downwardly, then come into the range of resiliently mounted lifting cams 158a and 158b engaging them from below (FIG. 27) and are rotated by the latter to the position visible in FIG. 7. Since one lifting cam 158 is disposed on each side of the central plane X, the drum cannot rotate, either. By the turning of the control cams 91, the selected front thread gripper 109b and the corresponding coding plate 106b are moved to the low positions visible in FIG. 7, while at the same time the other thread gripper 109a and the other coding plate 106a are correspondingly lifted to high positions. This shifting of the thread grippers 109 is possible at this moment because the rotation of the control lever 58 has caused the arresting slide 112 to be pulled forward so far that it is not in any of the transverse grooves 105 of the projections 103. The same movements are produced with regard to the thread gripper 109a if cam follower 152b is selected instead of cam follower 152a, because by means of the lift cams 158a and 158b, the thread gripper that is in front after the rotation of the drum 84 will be lowered. In both cases, the indentation 142 of the lowered thread gripper, and therefore also the thread end situated therein, is in the central plane X of the thread carrier, from which point the corresponding thread 16 is stretched upwardly at an angle to the corresponding thread eyelet 79, and underneath the range of rotation of the inserter 19.

Let it now be assumed that thread 16a has been selected for knitting and therefore the thread gripper 109a is forward. The thread carrier 18 now comes into the range of action of a second lifting ramp 159 of the cam 154 and of a second cam follower 160a and 160b, also represented in plan, for turning back the drum 84. Meantime, the cams followers 160a and 160b are disposed on both sides of the central plane X at a level corresponding to the low position of the coding plates 106, so that only cam follower 160a is active. The positions of the lifting ramp 159 and of cam followers 160a and 160b are otherwise so coordinated that the lifting ramp 159 first slightly raises the crank arm 63 so that the thread 16a can be gripped by the two outwardly projecting arms of the fork 74, and that then the drum 84 can be turned back and the crank arm 63 can be raised further. As soon as the rotation of the drum is completed, cam 154 ends, causing the catch 92 to lie again in the cradle 93. The arresting slide 112 is now disposed as in FIG. 4, so that upward and downward movement of the racks 99 is blocked.

When the control lever 58 swings back again, the thread 16a enters into the fork 74. On the one hand this tightens the thread portion that is between the thread gripper 109a and the thread eyelet 79a. On the other hand, the thread slips in the manner seen in FIG. 3 into the wedge-shaped groove 76 of the inserter 19, which is precisely at the level of the working section. From there the thread is stretched transversely of the transport direction R to the thread gripper 109a (FIG. 5), so that, in a known manner (German Offenlegungsschrift 30 03 570), it is caught by the first extended needle 13a of the opposite needle bed and can be brought to the correct position for insertion in the needles that follow.

After the thread 16a has been laid in the needles 13, the thread gripper 109a must again be opened to release the end of the thread. For this purpose the control station has lifting cams 161a and 161b which are represented in side elevation in FIG. 27 and in cross section in FIG. 6, and are disposed on both sides of the central plane X. The lifting cam 161a swings the laterally projecting actuating finger 128 of the thread gripper 109a upwardly, causing the spring clip 143 to move upwardly and gripping finger 141 downwardly, and the thread gripper is opened as seen in FIG. 3.

To prevent the other lifting cam 161b from acting in this process on the other thread gripper 109b which must remain closed, the lifting cams 161a and 161b have, as seen in FIGS. 6 and 27, a horizontal recess 163 extended up to a lifting ramp 162. The lifting cams 161 are dimensioned such that the free ends of the actuating fingers 128 of the thread carriers 109 which are in the middle or raised position (on the right in FIG. 6) enter into the recess 163 and therefore are not lifted. The free end of actuating finger 128 of a thread gripper situated in the low position (on the left in FIG. 6), however, first runs onto a broadened apex 164 of the lifting ramp 162 and is thereby slightly rotated. Since this rotation entails a rotation about the axis of the shift cam 124, the ends of the actuating fingers 128, which run against the apex 164 and then follow a circular path 165, upon reaching the recess 163, extend radially further outwardly than in the case of the actuating fingers 128 not affected by the apex 164, so that they then span the recess 163 and follow the cam 162. This completes the insertion of the corresponding thread 16a.

A special advantage of this system is that, by means of the lift portions 161 a distinction can be made between knitting and nonknitting thread carriers, and the lifting cams do not have to be controllable in order to avoid the opening of thread grippers 109 that carry a nonknitting thread.

The thread carriers carrying a knitting thread within the working range are carried, after leaving the operating area, through a control station whose cams and cam followers are represented in FIG. 28 in elevational views corresponding to FIG. 27. Essentially, the already described steps of operation take place in the reversed order.

The thread gripper 109a associated with the thread 16a being knitted runs in the manner indicated in FIG. 3 into the control station, being tensed in accordance with FIG. 4 between the last knitting needle 13b and the inserter 19, which is indicated only by a turn in the path of the thread so as to avoid confusion.

The control station has a cam 166 having a ramp 167 which lifts the crank arm 63 and thus the catch 92 from the cradle 93. Then the thread carrier comes into the range of two fixed cam followers 168a and 168b which are disposed at the level of the coding plate 106 which is in the raised position and affect only that coding plate. Consequently, in the example being described, only the coding plate 106b is operated by the cam follower 168b, resulting in a rotation of drum 84 by 90° to the position represented in FIG. 4. At the same time the crank arm 63 continues to be held up. Thus, after the drum 84 has rotated, the gripper jaws of the front thread gripper 109a is disposed above the section of thread held between the needle 13b and the inserter 19, but the corresponding gripping finger 141 is disposed below it. The thread gripper 109a must next be closed. Since the actuating finger 128 cannot be used since it is in the high position, the second actuating finger 130 disposed in another plane is aligned such that, if the actuating finger 128 is in the high position it extends downwardly. Since in this actuating finger must be rotated by about 90°, it is best to associate with it a second, radially shorter actuating finger 169 (FIG. 4) lying in the same plane. Two-lobed cams of appropriate shape 170a and 170b disposed on both sides of the central plane X (FIG. 28) can act on the actuating fingers 130 and 169. These cams contain a first ramp 171 which engages the actuating finger 130 and turns it by a part of its stroke. Then the actuating finger 169, which meantime has continued to turn and is now pointing vertically downward, encounters a second ramp 172 of cam 170, causing the thread gripper 109a to close completely. The cams 170 have no effect on the next thread gripper which is in the high position. When the thread gripper 109a is in the position seen in FIG. 4, the indentation 142 of gripping finger 141 is precisely underneath the thread, so that the thread enters the indentation in the closing movement.

After the closing of the thread gripper 109a, the cam 167 terminates, so that the crank arm 63 is rotated on the line 173 by the tension springs 119, and thus the fork 74 arrives at the position indicated in FIG. 7, in which it releases the piece of thread situated between the thread gripper 109a and the thread eyelet 79a. Then the piece of thread between the needle 13b and the thread gripper is severed, in a known manner. Parallel thereto, the two control cams 91 encounter cams 174 disposed on both sides of the central plane X and above their axes, which turn the control cams 91 back such that the two coding plates 106 again assume the same level, i.e., their center position. Lastly, the thread carrier 18 comes into range of rigid cams 174 provided on both sides. These cams do not act on the coding plates 106, but on the two holders 108 which are configured at their periphery just like the rear arms 151a and 151b, while the front arms 150a and 150b are lacking so as to avoid collision with the cam 175 that is inactive. At the same time, by means of another rising section 176 of cam 166, the crank arm 63 is raised, so that the catch 92 can lie on the cradle 93 and, at the end of cam 166, the locked, normal position of the thread carrier visible in FIG. 2 is reached. The fork 74 thus runs past the thread 16a, tensed outwardly from the corresponding thread gripper 109a, without catching it.

The thread carriers which do not knit with any of their threads could pass unaffected through the control station disposed at the end of the operating area, in accordance with FIG. 28. The result would be, however, that the width of the thread carriers measured across the central plane X when the drum is in the position visible in FIG. 4 would have to be at least just as great as the likewise measured width in the normal drum position visible in FIG. 2, since otherwise the thread carriers that are in the normal position could not pass through the space between the two cams 170 required for closing the thread grippers. Since the space available on a knitting machine is limited anyway, it is nevertheless desirable for the thread carrier in the position seen in FIG. 4 to have a smaller width than in the position seen in FIG. 2.

The invention therefore provides for pivoting also the nonknitting thread carriers when they pass the control station in accordance with FIG. 28. To this end, provision is made for configuring the cam follower 168 on one side of the central plane, e.g., cam follower 168b, such that it can only engage the coding plate 106b which is in the raised position, while the other cam, cam follower 168a for example, is so disposed and configured that it affects coding plate 106a entering both in the raised position and in the middle position. In this manner, the drums 84 of the thread carriers by which a thread is knitted are turned by the corresponding cam followers 168 active in the raised position, while the other cam follower 168 has no effect on account of the lowered other coding plate. The drum of a thread carrier knitting with no thread, however, is turned by the cam reaching the middle position, since its two coding plates 106 are in the middle position.

With regard to the return of these thread carriers, it is to be noted that, after passing through the space between the cams 170, in the case of those thread carriers which carry a knitting thread, the forks 74 are still swung back (line 173) before the turning-back (cam follower 175) takes place. This swing-back is not desired for the nonknitting thread carriers, because their thread, which after the rotation lies forward, applies itself from without against the still not-swung fork 74 and therefore can be caught by it when it swings. Therefore an additional cam, not shown, is provided in the control station in accordance with FIG. 28, which immediately turns the drums 84 of the nonknitting thread carriers partially back after they have run past the cams 170, in order to arrange the thread outside of the range of action of the fork. This cam is disposed on the necessary side of the central plane X and acts on the coding plate 206, which is in the middle position, of the nonknitting thread carrier. The complete turnback of the nonknitting thread carriers is then produced, as in the case of the knitting thread carriers, by the cam follower 175, since the cradle 93 has not been lowered sufficiently for the catch 92 until it is reached.

The invention is not limited to the embodiment described. This is especially true of the arrangement and configuration of the various parts of the thread carriers and of the control stations, since in this regard attention has been given to a small, space-saving design for the purpose of achieving as great a number of systems as possible on the knitting machine.

Furthermore, it is not necessary to provide the described thread carrier basically with two threads. Alternatively, each thread carrier can be provided for carrying only one thread, in which case either one thread gripper remains unoccupied, or all of the parts provided for the feeding of a second thread are omitted. In this kind of application, too, the corresponding thread carrier can be threaded into the passage or withdrawn from it, in order thereby to distinguish knitting thread carriers from nonknitting thread carriers.

Lastly, the lifting cams 161 acting on the actuating fingers 128 can be displaceable along the needle beds and in some cases they can be automatically operated, so that individual needles can be adjusted to the first knitting needle when the width of the knit goods is increased or decreased.

I claim:

1. Thread carrier for a knitting machine, having an inserter (19) which is in the form of an open channel (76) at its extremity where the thread (16) emerges, and having at least one controllable thread gripper, characterized in that the inserter (19) and the thread gripper (109) are disposed movably relative to one another such that the thread can either be inserted into the channel (76) or removed therefrom by the thread gripper (109) itself.

2. Thread carrier of claim 1, characterized in that the thread gripper (109) is mounted on a rotatable drum (84).

3. Thread carrier of claim 2, characterized in that a shaft (89) disposed transversely of the axis of the drum (84) and provided at least at one end with a control cam (91) passes through the drum (84).

4. Thread carrier of claim 2, characterized in that the thread gripper (109) is fastened to a rack (99) mounted for displacement parallel to the axis of the drum (84).

5. Thread carrier of claim 4, characterized in that the rack (99) has at least one tooth (101) which engages a tooth gap (97) formed on the shaft (89).

6. Thread carrier of claim 4, characterized in that a coding plate (106) is fastened to one end of the rack (99) projecting from the drum (84).

7. Thread carrier of claim 1, characterized in that the inserter (19) is fastened to one arm (61) of a control lever (58) pivotally mounted on a pivot pin (66).

8. Thread carrier of claim 6, characterized in that on the end of the rack (99) provided with the coding plate (106) a transverse groove (105) is formed, and the control lever (58) has a second arm (60) which is articulated to an arresting slide (112) which cooperates with the transverse groove (105), is displaceably mounted, and is intended for the locking of the rack (99).

9. Thread carrier of claim 1, characterized in that the thread gripper (109) has two slides (133, 134) which are displaceable in opposite, parallel directions by a shifting cam (124), one of which is provided with a gripping finger (141) and the other is coupled with a gripping spring (143) which has at least one gripping jaw (147) cooperating with the gripping finger (141).

10. Thread carrier of anyone of claims 5 to 9, characterized in that it has two similarly configured thread grippers (109a, 109b) which are disposed symmetrically on both sides of a plane laid through the axis of the drum (84) and are fastened each to a rack (99) parallel to the drum axis, and that each rack (99) has at least one tooth (101) which engages one of two diametrically opposite tooth gaps (97) in the shaft (89).

11. Thread carrier of claim 7, characterized in that on the end of the rack (99) provided with the coding plate (106) a transverse groove (105) is formed, and the control lever (58) has a second arm (60) which is articulated to an arresting slide (112) which cooperates with the transverse groove (105), is displaceably mounted, and is intended for the locking of the rack (99).

* * * * *